US012006281B2

(12) United States Patent
Li et al.

(10) Patent No.: US 12,006,281 B2
(45) Date of Patent: Jun. 11, 2024

(54) SYSTEMS AND METHODS FOR CO-PRODUCING XYLITOL AND CARAMEL PIGMENT BY UTILIZING XYLOSE MOTHER LIQUID

(71) Applicant: ZHEJIANG HUAKANG PHARMACEUTICAL CO., LTD., Zhejiang (CN)

(72) Inventors: Mian Li, Quzhou (CN); Weidong Xu, Quzhou (CN); Deshui Chen, Quzhou (CN); Xinping Cheng, Quzhou (CN); Chengjun Liao, Quzhou (CN); Qiang Wu, Quzhou (CN); Wulong Yang, Quzhou (CN); Shufang Qin, Quzhou (CN)

(73) Assignee: ZHEJIANG HUAKANG PHARMACEUTICAL CO., LTD., Quzhou (CN)

( * ) Notice: Subject to any disclaimer, the term of this patent is extended or adjusted under 35 U.S.C. 154(b) by 0 days.

(21) Appl. No.: 18/348,509

(22) Filed: Jul. 7, 2023

(65) Prior Publication Data
US 2023/0348350 A1 Nov. 2, 2023

Related U.S. Application Data

(63) Continuation-in-part of application No. PCT/CN2022/125220, filed on Oct. 13, 2022.

(30) Foreign Application Priority Data

Dec. 29, 2021 (CN) .......................... 202111644482.0

(51) Int. Cl.
*C07C 29/141* (2006.01)
*C07C 29/78* (2006.01)
(Continued)

(52) U.S. Cl.
CPC ............ *C07C 29/88* (2013.01); *C07C 29/141* (2013.01); *C07C 29/78* (2013.01); *C07C 29/90* (2013.01);
(Continued)

(58) Field of Classification Search
CPC ......... C07C 29/78; C07C 29/88; C07C 29/90; C07C 29/141; C07C 31/18; C09B 67/006; B01D 2311/04
See application file for complete search history.

(56) References Cited

FOREIGN PATENT DOCUMENTS

| CN | 101823939 A | 9/2010 |
| CN | 101857523 A | 10/2010 |

(Continued)

OTHER PUBLICATIONS

International Search Report in PCT/CN2022/125220 dated Jan. 12, 2023, 7 pages.
(Continued)

*Primary Examiner* — Yate' K Cutliff
(74) *Attorney, Agent, or Firm* — METIS IP LLC

(57) ABSTRACT

The embodiment of the present disclosure provides a system for co-producing a xylitol and a caramel pigment by utilizing a xylose mother liquid, including an extraction assembly, a refined hydrogenation assembly and a browning reaction assembly. The extraction assembly is configured to obtain an extracted liquid and a raffinate liquid respectively by performing an initial extraction on the xylose mother liquid; the refined hydrogenation assembly is configured to prepare a crystal xylitol by performing a refined hydrogenation process on the extracted liquid; the browning reaction assembly is configured to prepare the caramel pigment by performing a browning reaction process on the raffinate liquid.

2 Claims, 3 Drawing Sheets

(51) Int. Cl.
*C07C 29/88* (2006.01)
*C07C 29/90* (2006.01)
*C09B 67/20* (2006.01)

(52) U.S. Cl.
CPC ........ C09B 67/006 (2013.01); *B01D 2311/04* (2013.01)

(56) References Cited

FOREIGN PATENT DOCUMENTS

| | | | | |
|---|---|---|---|---|
| CN | 102241707 A | 11/2011 | | |
| CN | 103409315 A | 11/2013 | | |
| CN | 106591384 A | 4/2017 | | |
| CN | 107893132 A | 4/2018 | | |
| CN | 109503676 A | * 3/2019 | ........... | C07C 29/141 |
| CN | 109503676 A | 3/2019 | | |
| CN | 113214531 A | 8/2021 | | |
| CN | 114213215 A | 3/2022 | | |

OTHER PUBLICATIONS

Notification to Grant Patent Right for Invention in Chinese Application No. 202111644482.0 dated Sep. 24, 2023, 2 pages.
First Office Action in Chinese Application No. 202111644482.0 dated Apr. 3, 2023, 14 pages.

\* cited by examiner

SYSTEMS AND METHODS FOR CO-PRODUCING XYLITOL AND CARAMEL PIGMENT BY UTILIZING XYLOSE MOTHER LIQUID

CROSS-REFERENCE TO RELATED CLAIMS

The present disclosure is a continuation in part of International Application No. PCT/CN2022/125220, field on Oct. 13, 2022, which claims priority of Chinese Patent Application No. 202111644482.0, filed on Dec. 29, 2021, the entire contents of which are hereby incorporated by reference.

TECHNICAL FIELD

The present disclosure relates to the technical field of utilizing xylose mother liquid, and in particular, to a system and method for co-producing a xylitol and a caramel pigment by utilizing a xylose mother liquid.

BACKGROUND

The production of xylitol mostly uses corncobs, corn stalks, etc. as raw materials. Xylose is extracted from the raw materials, and then the xylose is hydrogenated to prepare the xylitol. However, a xylose component content in xylose mother liquid obtained after the xylose is extracted is still very high. If the xylose component in the xylose mother liquid can be reused, it will be more conducive to utilizing resources and energy.

Therefore, it is desirable to provide a system and method for co-producing xylitol and caramel pigment by utilizing xylose mother liquid, which can fully utilize the value of the xylose mother liquid.

SUMMARY

One of the embodiments of the present disclosure provides a system for co-producing a xylitol and a caramel pigment by utilizing a xylose mother liquid. The system may include an extraction assembly, a refined hydrogenation assembly, and a browning reaction assembly. The extraction assembly may be configured to obtain an extracted liquid and a raffinate liquid respectively by performing an initial extraction on the xylose mother liquid. The refined hydrogenation assembly may be configured to prepare a crystal xylitol by performing a refined hydrogenation process on the extracted liquid. The browning reaction assembly may be configured to prepare the caramel pigment by performing a browning reaction process on the raffinate liquid.

One of the embodiments of the present disclosure provides a method for co-producing a xylitol and a caramel pigment by utilizing a xylose mother liquid, which uses the system for co-producing a xylitol and a caramel pigment by utilizing a xylose mother liquid. The method may include: obtaining the extracted liquid and the raffinate liquid by performing, by the extraction assembly, the initial extraction on a raw material of the xylose mother liquid; obtaining the crystal xylitol by performing, by the refined hydrogenation assembly, the refined hydrogenation process on the extracted liquid; obtaining the caramel pigment by performing, by the browning reaction assembly, the browning reaction process on the raffinate liquid.

BRIEF DESCRIPTION OF THE DRAWINGS

The present disclosure will be further illustrated by way of exemplary embodiments, which will be described in detail with accompanying drawings. These embodiments are non-limiting, and in these embodiments, a same number indicates a same structure, wherein.

DETAILED DESCRIPTION

Figure 1:
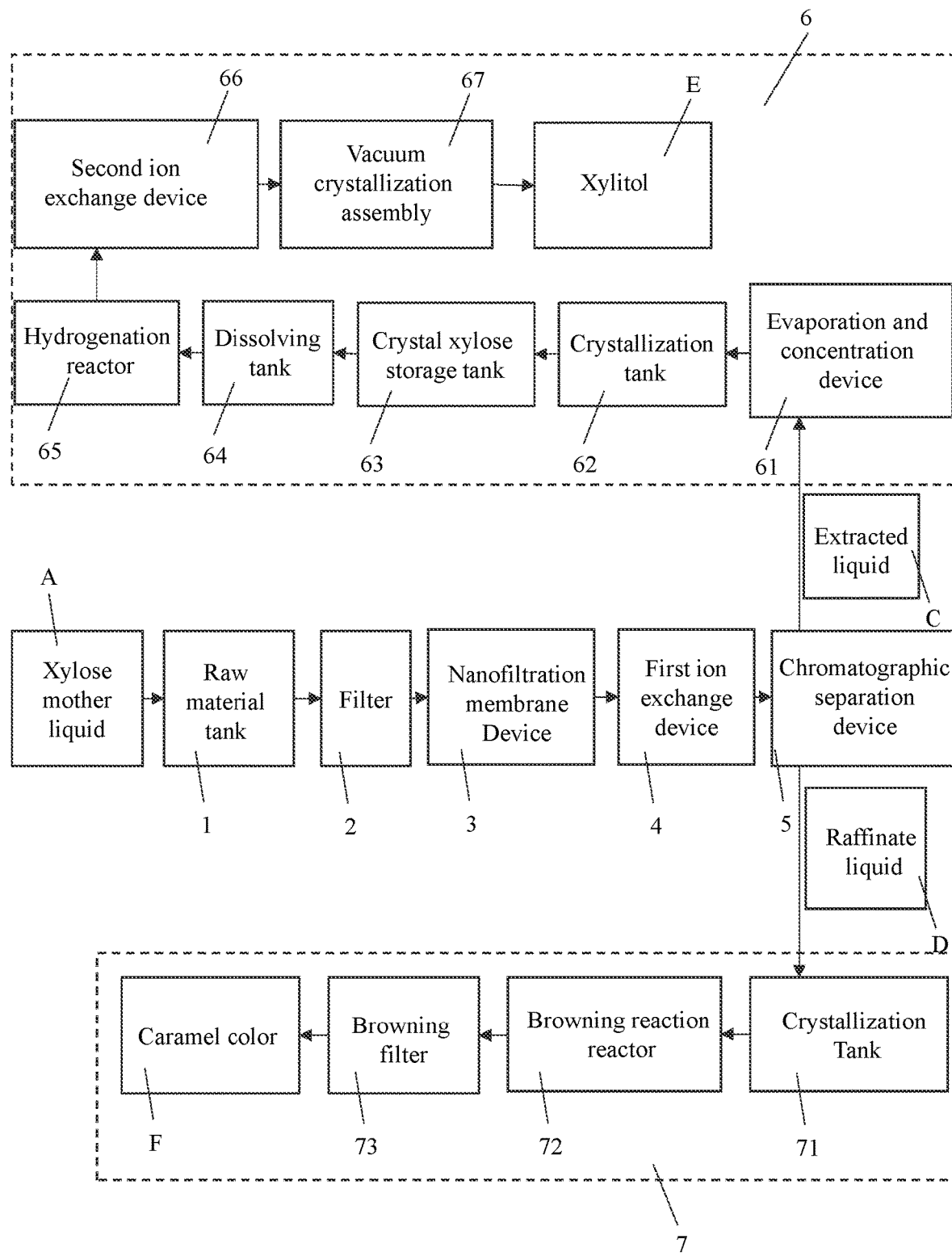
FIG. 1 is a schematic diagram illustrating an exemplary system for co-producing a xylitol and a caramel pigment by utilizing a xylose mother liquid according to some embodiments of the present disclosure.

In order to illustrate technical solutions of the embodiments of the present disclosure more clearly, the following briefly introduces the drawings that need to be used in the description of the embodiments. Apparently, the accompanying drawings in the following description are only some examples or embodiments of the present disclosure, and those skilled in the art may also apply the present disclosure to other similar scenarios. Unless obviously obtained from the context or the context illustrates otherwise, the same numeral in the drawings refers to the same structure or operation.

It should be understood that "system," "device," "unit," and/or "module" as used herein is a manner for distinguishing different components, elements, parts, parts, or assemblies of different levels. However, the words may be replaced by other expressions if other words can achieve the same purpose.

As indicated in the present disclosure and claims, the terms "a," "an," "one," and/or "the" are not specific to the singular and may include the plural unless the context clearly indicates an exception. Generally speaking, the terms "including" and "comprising" only suggest the inclusion of clearly identified steps and elements, and these steps and elements do not constitute an exclusive list, and the method or device may also contain other steps or elements.

Flowcharts are used in the present disclosure to illustrate the operations performed by the system according to the embodiments of the present disclosure. It should be understood that the preceding or following operations are not necessarily performed in the exact order. Instead, various steps may be processed in reverse order or simultaneously. At the same time, other operations can be added to these procedures, or a certain step or steps can be removed from these procedures.

The xylose component content in a xylose mother liquid is very high, and the preparation of xylitol often cannot make full use of the xylose component in the xylose mother liquid, resulting in a waste of resources and energy. Therefore, it is desirable to effectively utilize a remaining xylose component while utilizing the xylose mother liquid to extract and prepare the xylitol.

Based on this, in some embodiments of the present disclosure, a system for co-producing a xylitol and a caramel pigment by utilizing a xylose mother liquid may perform an initial extraction on the xylose mother liquid by an extraction assembly; prepare a crystal xylitol by performing a refined hydrogenation process on an extracted liquid by a refined hydrogenation assembly; preparing a caramel pigment by performing a browning reaction process on a raffinate liquid by a browning reaction assembly, which can give full play to the value of the xylose mother liquid.

Figure 2:
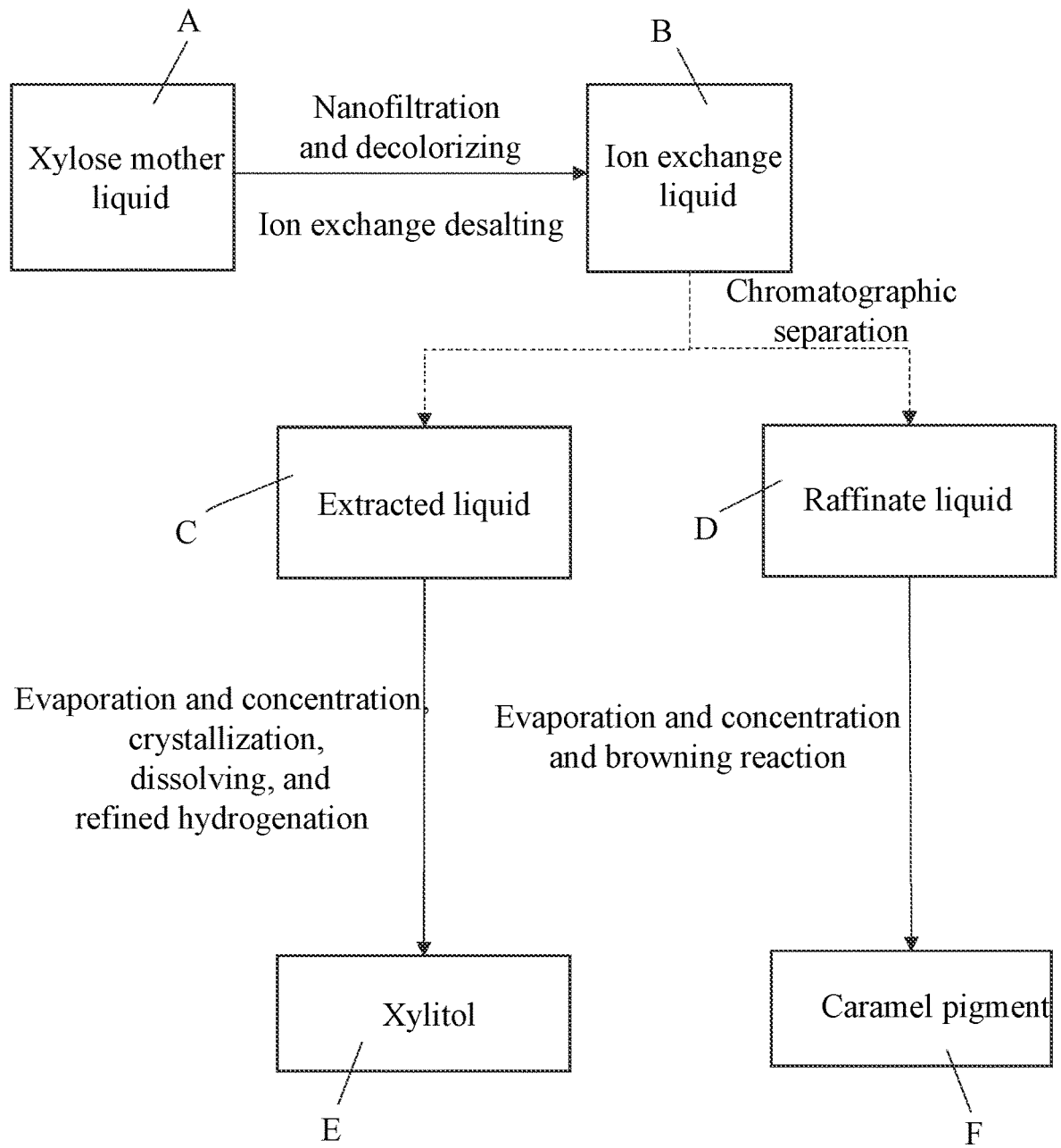
FIG. 2 is a flowchart illustrating an exemplary process for co-producing a xylitol and a caramel pigment by utilizing a xylose mother liquid according to some embodiments of the present disclosure.

FIG. 1 is a schematic diagram illustrating an exemplary system for co-producing a xylitol and a caramel pigment by utilizing a xylose mother liquid according to some embodiments of the present disclosure. FIG. 2 is a flowchart illustrating an exemplary process for co-producing a xylitol and a caramel pigment by utilizing a xylose mother liquid according to some embodiments of the present disclosure.

In some embodiments, the system for co-producing a xylitol and a caramel pigment by utilizing a xylose mother liquid may include an extraction assembly, a refined hydrogenation assembly 6, and a browning reaction assembly 7.

The extraction assembly may be configured to perform an initial extraction on the xylose mother liquid. The extraction assembly may include multiple devices for processing the xylose mother liquid and extracting a desired substance from the xylose mother liquid. For example, an extracted liquid with a higher xylose component content may be extracted from the xylose mother liquid, and a remaining liquid from the xylose mother liquid may be extracted as the raffinate liquid. The raffinate liquid may still contain certain xyloses, but the xylose component content in the raffinate liquid may be lower than the xylose component content in the extracted liquid. In some embodiments, the extraction assembly may sequentially filter, decolorize, desalt, and chromatographically separate the xylose mother liquid to obtain the extracted liquid and the raffinate liquid. For details, please refer to the relevant description below.

The refined hydrogenation assembly 6 may be configured to perform the refined hydrogenation process on an extracted liquid of a xylose mother liquid A to prepare a crystal xylitol E.

The browning reaction assembly 7 may be configured to perform the browning reaction process on a raffinate liquid D to prepare a caramel pigment F.

As shown in FIG. 1 and FIG. 2, in some embodiments, the extraction assembly may include a raw material tank 1, a filter 2, a nanofiltration membrane device 3, a first ion exchange device 4, and a chromatographic separation device 5 that are connected in sequence through a pipeline.

The raw material tank 1 refers to a container for storing the xylose mother liquid A. The shape of the raw material tank 1 may include various types. For example, the shape of the raw material tank 1 may be cylindrical or cubic. The material of the raw material tank 1 may include stainless steel, alloy, or plastic. The shape and the material of the raw material tank 1 are not limited herein.

The filter 2 refers to a device for filtering impurities in the xylose mother liquid A. For example, the filter 2 may include a metal mesh with pores, a ceramic filter, or the like.

The nanofiltration membrane device 3 refers to a device for decolorizing the xylose mother liquid A. For example, the nanofiltration membrane device 3 may include one or more membrane materials with nanoscale pores.

In some embodiments, the nanofiltration membrane device 3 may be configured to decolorize the xylose mother liquid A that flows through the nanofiltration membrane device 3 to obtain a retentate liquid and a permeation liquid. The retentate liquid may be a pigment liquid and the permeation liquid may be a decolorized liquid.

The first ion exchange device 4 may be configured to perform an ion exchange reaction to desalt the decolorized liquid. For example, the first ion exchange device 4 may include an ion exchange resin.

In some embodiments, the first ion exchange device 4 may desalt the decolorized liquid that flows through the first ion exchange device 4 to obtain an ion exchange liquid B.

The chromatographic separation device 5 refers to a device for a chromatographic separation of the ion exchange liquid B. Merely by way of example, the chromatographic separation device 5 may include a chromatographic column filled with different fillers inside, such as a polar liquid organics or a non-polar liquid organics, so as to separate different components of the ion exchange liquid B.

In some embodiments, the chromatographic separation device 5 may be configured to perform a chromatographic separation on the ion exchange liquid B that flows through the chromatographic separation device 5 to obtain an extracted liquid C and a raffinate liquid D. The xylose component content in the extracted liquid C may be higher than the xylose component content in the raffinate liquid D.

In some embodiments, the extraction may be performed on the xylose mother liquid A by the extraction assembly as follows. The impurities in the xylose mother liquid A may be fully filtered by the filter 2, components such as pigment may be filtered after a nanofiltration process is performed by the nanofiltration membrane device 3, the desalination may be realized through an ion exchange reaction performed by the first ion exchange device 4, and the extracted liquid C with the higher xylose component content may be obtained through the chromatographic separation performed by the chromatographic separation device 5, which can ensure the purity of xylose and improve a production yield rate of the xylitol subsequently. The remaining mixed liquid after the extracted liquid C is extracted by the extraction assembly may be the raffinate liquid D, which is subsequently further processed to achieve full utilization.

As shown in FIG. 1, in some embodiments, the refined hydrogenation assembly 6 may include an evaporation and concentration device 61, a crystallization tank 62, a crystal xylose storage tank 63, a dissolving tank 64, a hydrogenation reactor 65, a second ion exchange device 66, and a vacuum crystallization assembly 67.

The evaporation and concentration device 61 refers to a device that concentrates the extracted liquid through evaporation. In some embodiments, the evaporation and concentration device 61 may include a heater and a cooler. The heater may heat the extracted liquid and convert the extracted liquid into steam, and the cooler may cool and concentrate the steam of the extracted liquid.

The crystallization tank 62 refers to a device for crystallizing the xylose to obtain a crystal xylose. For example, a xylose solution may be supersaturated and crystallized by adjusting a temperature inside the crystallization tank 62.

The crystal xylose storage tank 63 refers to a device for storing the crystal xylose. In some embodiments, the crystal xylose storage tank 63 may include a stainless-steel tank with a silicone seal, which has moisture-proof and oxidation-proof properties.

The dissolving tank 64 refers to a device for dissolving the crystal xylose into a liquid and storing the liquid. For example, water may be added to the dissolving tank 64 to dissolve the crystal xylose into a xylose liquid.

The hydrogenation reactor 65 refers to a device configured for a hydrogenation reduction reaction of the xylose liquid to generate the xylitol. For example, the hydrogenation reactor 65 may include a thick-walled steel tank capable of withstanding high temperature and high pressure.

The second ion exchange device 66 refers to a device configured to remove anions and cations in a xylitol liquid. For example, the second ion exchange device 66 may include the ion exchange resin, and the anions and the cations in the xylitol liquid may be removed by flowing through the ion exchange resin.

The vacuum crystallization assembly 67 refers to a device for crystallizing the xylitol solution that is processed by the ion exchange device 66 in a vacuum environment to obtain the crystal xylitol E. For example, the vacuum crystallization component 67 may make the xylitol solution supersaturated and crystallized by performing solvent adiabatic evaporation and solution cooling on the xylitol solution simultaneously in the vacuum environment.

In some embodiments, the evaporation and concentration, the crystallization, the dissolution, the ion exchange, the hydrogenation reaction, and the vacuum crystallization may be realized by the refined hydrogenation assembly 6, thereby preparing the xylose after purification into the xylitol, and further refining an obtained xylitol.

As shown in FIG. 1, in some embodiments, the browning reaction assembly 7 may include a concentration tank 71, a browning reaction reactor 72, and a browning filter 73.

The concentration tank 71 refers to a device for concentrating the raffinate liquid D, and the raffinate liquid D may be concentrated to a preset concentration range and stored as required. For example, the concentration tank 71 may concentrate the raffinate liquid D through evaporation or boiling.

The browning reaction reactor 72 refers to a device configured for a browning reaction of the raffinate liquid D to produce the caramel pigment F. In some embodiments, the browning reaction reactor 72 may include a heating and pressurizing device for adjusting a temperature and pressure required for the browning reaction.

The browning filter 73 refers to a device for filtering solid impurities in the caramel pigment F. For example, the browning filter 73 may be composed of multiple layers of filtering materials with different pore sizes.

In some embodiments, through technological processes of the evaporation and concentration, the browning reaction, and the filtering process of the xylose mother liquid, the raffinate D after the xylose mother liquid is extracted can be processed to obtain the caramel pigment F, thereby realizing the full utilization of the xylose mother liquid.

In some embodiments, the system can be used for co-producing the xylitol and the caramel pigment by utilizing the xylose mother liquid, and a method for co-producing a xylitol and a caramel pigment by utilizing a xylose mother liquid includes following steps.

The extracted liquid C and the raffinate liquid D may be obtained by performing an initial extraction, by the extraction assembly, a raw material of the xylose mother liquid A.

The crystal xylitol E may be obtained by performing, by the refined hydrogenation assembly 6, a refined hydrogenation process on the extracted liquid C.

The caramel pigment F may be obtained by performing, by the browning reaction assembly 7, a browning reaction process on the raffinate liquid D.

In some embodiments, the method for co-producing a xylitol and a caramel pigment by utilizing a xylose mother liquid may further includes following steps.

In step 1, the raw material of the xylose mother liquid A in the raw material tank 1 may be transported to the filter 2 through a pipeline for filtering impurities, and then filtered xylose mother liquid A may be transported to the nanofiltration membrane device 3 for a decolorizing process. In some embodiments, the step 1 corresponds to certain afore-mentioned steps of the initial extraction of the raw material of the xylose mother liquid A through the extraction assembly.

In some embodiments, the xylose mother liquid A may be a by-product obtained after the xylose component is extracted from a biomass raw material during a process of using the xylose to prepare the xylitol. In some embodiments, a mass percentage concentration of a dry matter of the xylose mother liquid A, that is, a sugar concentration, may be 50 to 60 wt %. In the dry matter, a content of glucose may be 12 to 18 wt %, a content of xylose may be 40 to 50 wt %, a content of arabinose may be 17 to 23 wt %, a content of mannose may be 10 to 22 wt %, and a content of galactose may be 0 to 6 wt %.

In some embodiments, during the decolorizing process, an operating temperature of the nanofiltration membrane device 3 may be set between 340 to 48° C., an operating pressure of the nanofiltration membrane device 3 may be set between 25 bar to 35 bar, and a yield rate of the nanofiltration membrane device 3 may reach 90% to 98%.

In step 2, the raw material of the xylose mother liquid after the decolorizing process may be transported to the first ion exchange device 4 for a desalting process to obtain an ion exchange liquid. In some embodiments, the step 2 corresponds to certain aforementioned steps of the initial extraction of the raw material of the xylose mother liquid A through the extraction assembly.

In some embodiments, during the desalting process, an electrical conductivity may be controlled being smaller than 50 us/cm, and a yield rate may reach 90% to 98%.

In step 3, the ion exchange liquid may be transported to the chromatographic separation device 5 for a chromatographic separation process, and after the chromatographic separation process, the extracted liquid C and the raffinate D may be obtained. The xylose component content in the extracted liquid C may be higher than the xylose component content in the raffinate liquid D. The extracted liquid C may be transported to the refined hydrogenation assembly 6 for the refined hydrogenation process to obtain the crystal xylitol E with a purity over 99%, and the raffinate liquid D may be subjected to the browning reaction process through the browning reaction assembly 7 to prepare the caramel pigment F. In some embodiments, the step 3 corresponds to certain aforementioned steps of the initial extraction of the raw material of the xylose mother liquid A through the extraction assembly, corresponds to the step of performing the refined hydrogenation process on the extracted liquid through the refined hydrogenation assembly, and corresponds to the step of performing the browning reaction process on the raffinate liquid D through the browning reaction assembly.

In some embodiments, the refined hydrogenation process may include: concentrating the extracted liquid C through the evaporation and concentration device 61; obtaining the crystal xylose through crystallization in the crystallization tank 62; obtaining the xylose liquid by dissolving the crystal xylose with water; controlling a refraction of the xylose liquid being 50% to 60% and a pH value of the xylose liquid being 5.00 to 7.00; adding a nickel catalyst with a mass percentage of 0.01% to 0.02% into the xylose liquid; controlling a reaction temperature of the browning reaction between 130° C. to 140° C. and a steam pressure above 0.4 MPa; and performing a hydrogenation reaction. A pressure of the hydrogenation reaction may be controlled being between 7.0 MPa to 9.5 MPa and a time of the hydrogenation reaction may be controlled being 60 minutes to 120 minutes.

In some embodiments, the refined hydrogenation process may include: transporting the extracted liquid C after evaporation and concentration to the crystallization tank 62 for crystallization; obtaining the xylose liquid by dissolving a crystal xylose obtained through the crystallization with water; obtaining a xylitol solution by transporting the xylose liquid to the hydrogenation reactor 65 for the hydrogenation reaction; settling the xylitol solution to remove a catalyst; obtaining a supernatant after settling the xylitol solution; removing anions and cations from the supernatant by adopting the second ion exchange device 66; performing a vacuum evaporation and concentration by using the vacuum crystallization assembly 67; performing a vacuum boiling of sugar and crystallization to precipitate a crystal; and obtaining the crystal xylitol by performing a centrifugation operation and a drying operation on the crystal.

In some embodiments, the browning reaction process may include: concentrating the raffinate liquid D to a refraction between 75% to 85% and a pH value between 7.00 to 9.00; adding a compounded amino compound with a mass percentage of 6% to 12% to the concentrated raffinate liquid D as a catalyst; and performing the browning reaction. A reaction temperature of the browning reaction may be controlled being between 120° C. to 140° C. and a time of the browning reaction may be controlled being 60 minutes to 240 minutes. In some embodiments, the compounded amino compound may be compounded with urea and ammonium carbonate with a compounding ratio being 1:2 to 2:1.

In some embodiments, the browning reaction process may include: obtaining the caramel pigment F by performing a concentration process, a browning reaction process, and a filtering process on the raffinate liquid D. The caramel pigment F may be in a liquid form, a red index of the caramel pigment F may be over 7, and an absorbance of the caramel pigment F at 610 nm may be over 0.07.

In some embodiments of the present disclosure, the extracted liquid and the raffinate liquid of the xylose mother liquid may be prepared to obtain the crystal xylitol and the caramel pigment respectively. By accurately controlling an operating condition, a desalting process condition, a refined hydrogenation process condition, and a browning reaction condition of the nanofiltration membrane device 3, the purity of the crystal xylitol can be effectively improved. By utilizing the raffinate liquid, the full utilization of the xylose mother liquid can be achieved, which improves the production efficiency, and reduces the waste, thereby having a strong economic value.

A following embodiment 1 and a comparative embodiment 1 further illustrate the system and method for co-producing a xylitol and a caramel pigment by utilizing a xylose mother liquid.

Embodiment 1

The raw material of the xylose mother liquid A with a refraction of 60 wt % in the raw material tank 1 was transported to filter 2 by a pipeline for filtering impurities, and then transported to the nanofiltration membrane device 3 for the decolorizing process. The operating temperature of nanofiltration membrane device 3 was 45° C. and the operating pressure was 30 bar. The decolorized raw material of the xylose mother liquid A was transported to the first ion exchange device 1 for the desalting process, and the electrical conductivity rate was controlled being smaller than 50 us/cm. The ion exchange liquid processed by the first ion exchange device 1 was transported to the chromatographic separation device 5 for the chromatographic separation process. Then the extracted liquid C with a high xylose component content obtained after the chromatographic separation process was transported for a refinement process, a crystallization process, and a hydrogenation process to obtain the crystal xylitol E with a purity over 99%. The raffinate liquid D with a low xylose component content obtained after the chromatographic separation was transported for a browning reaction. The yield rate of the decolorizing and desalting processes reached 95%, and a yield rate of the crystal xylose was 48%. The extracted liquid C obtained through evaporation and concentration after the chromatographic separation was transported to the crystallization tank 62, and the crystallized crystal xylose was dissolved with water to obtain the xylose liquid. The refraction of the xylose liquid was controlled between 50% to 60% and the pH value was controlled between 5.00 to 7.00. The nickel catalyst with a mass percentage of 0.01% to 0.02% was added into the xylose liquid. The reaction temperature was controlled at 135° C. and the steam pressure was controlled above 0.4 MPa. Then the xylose liquid was transported to the hydrogenation reactor 65 for the hydrogenation reaction. The pressure of the hydrogenation reaction was controlled at 8 MPa and the time of the hydrogenation reaction was 90 minutes. The xylitol solution obtained after the hydrogenation reaction was completed was settled to remove the catalyst, and a hydrogenated liquid obtained was desalted by the second ion exchange device 66. A desalted liquid was processed by the vacuum crystallization assembly 67 to precipitate the crystal xylitol E, and then the crystal xylitol E with a purity of 99% was obtained through a centrifugation operation and a drying operation. The raffinate liquid D was concentrated to a refraction of 80% and the pH value of the raffinate liquid D was adjusted to 9.00. The compounded amino compound (compounded by the urea and the ammonium carbonate with a compounding ratio of 1:2) with a mass percentage of 9% was added as a catalyst. A reaction temperature of the browning reaction was controlled at 120° C. and a time of the browning reaction was controlled to be 240 minutes. Then, a caramel pigment F liquid was obtained. The color ratio of the caramel pigment F liquid was 20,000 EBC, the red index of the caramel pigment F liquid was 7.1, and the absorbance of the caramel pigment F liquid at 610 nm was 0.078.

In the embodiment, the utilization rate of a reducing sugar in the raffinate liquid D reached 70% (calculated on a dry basis). The utilization rate refers to a ratio of a consumption of reducing sugar for the browning reaction to a total amount of reducing sugar of the mother liquid of the extracted liquid.

In the embodiment, a value of the caramel pigment prepared by the raffinate liquid is relatively higher, which is significantly higher than a value of the raffinate liquid, and the value of the raffinate liquid processed by the browning reaction has been significantly improved.

Comparative Embodiment 1

The xylose mother liquid was directly utilized to produce the xylitol, the steps of which are as follows. A raw material of the xylose mother liquid with a refraction of 60 wt % in the raw material tank 1 was transported to the filter 2 through the pipeline for the filtering process, and then activated carbon with a mass percentage of 0.5% was added to a decoloring tank for the decolorizing processing. After the decolorizing process, a plate and frame filter press was performed, and a filtrate was transported to the first ion exchange module 4 for the desalting process. The yield rate of the decoloring and desalting was 85%. Then after the chromatographic separation, the concentration and evaporation, the crystallization and the centrifugation operation, the yield rate of the crystal xylose was 45% (calculated on a dry basis). The xylitol was prepared after the hydrogenation process. A large amount of the raffinate liquid had not been effectively utilized and was finally processed as a mixed syrup. A price of the mixed syrup is 1,500 yuan per ton, and the value of the raffinate liquid cannot be increased.

In summary, the yield rate of the crystal xylose can be increased from 45% to 48% through the nanofiltration, the decolorizing process, and the ion exchange desalting process. By a high-value utilization of the raffinate liquid, the raffinate liquid with a relatively low value can be converted into a caramel pigment with a relatively high value, which greatly improves the value of the xylose mother liquid.

In some embodiments, the browning reaction assembly 7 may further include a detection device. The detector device may be configured to detect a sample of the raffinate liquid D obtained by the chromatographic separation device 5 before preparing the caramel pigment, so as to obtain main ingredient content data of the raffinate liquid D. In some embodiments, the main ingredient of the raffinate liquid D may include the reducing sugar.

In some embodiments, the detection device may include a conductivity meter. The conductivity meter may be used to detect a conductivity rate of the raffinate liquid D, so as to determine the component content of the reducing sugar in the raffinate liquid D.

In some embodiments, since the caramel pigment can be prepared by the reducing sugar, the quality of the caramel pigment may be predicted by detecting the component content of the reducing sugar in the raffinate liquid D.

In some embodiments, the system for co-producing a xylitol and a caramel pigment by utilizing a xylose mother liquid may further include a processor. In some embodiments, the processor may include one or more processing engines (e.g., a single-chip processing engine or a multi-chip processing engine).

In some embodiments, the processor may be configured to obtain the main ingredient content data of the raffinate liquid D detected by the detection device; determine a first predicted quality of the caramel pigment based on the main ingredient content data; determine target preparation parameter(s) by adjusting preset preparation parameter(s) based on the first predicted quality and a target quality. The preset preparation parameter may be determined based on a preferred parameter range. For example, the preset preparation parameter may be a most frequently-used parameter within the preferred parameter range.

The first predicted quality refers to an index for evaluating the quality of the caramel pigment. The first predicted quality may include a quality distribution of multiple regions in multiple devices, for example, a predicted quality distribution of multiple regions in the concentration tank 71 and the browning reactor 72.

In some embodiments, the first predicted quality of the caramel pigment may include at least one of a color ratio, a red index, an absorbance at 610 nm, or the like.

The target quality refers to a quality index that the caramel pigment needs to achieve. Corresponding to the predicted quality, the target quality may also include at least one of a target color ratio, a target red index, a target absorbance at 610 nm, etc.

In some embodiments, the target quality may be preset by the system or manually.

In some embodiments, the processor may determine the first predicted quality of the caramel pigment by a vector retrieval based on the main ingredient content data. For example, the processor may construct a vector to be matched based on the main ingredient content data. The processor may obtain a reference vector reference vector whose vector distance from the vector to be matched satisfies a distance threshold by searching in a vector database based on the vector to be matched. Then, the processor may determine a historical quality corresponding to the reference vector as the first predicted quality. The vector database may be configured to store several historical vectors and historical qualities corresponding to the several historical vectors. The historical vector may be determined based on the main ingredient content data.

In some embodiments, the processor may also determine the first predicted quality of the caramel pigment based on a quality model.

In some embodiments, the processor may generate the first predicted quality of the caramel pigment using the quality model based on the main ingredient content data of the raffinate liquid D and the preset preparation parameter.

Figure 3:
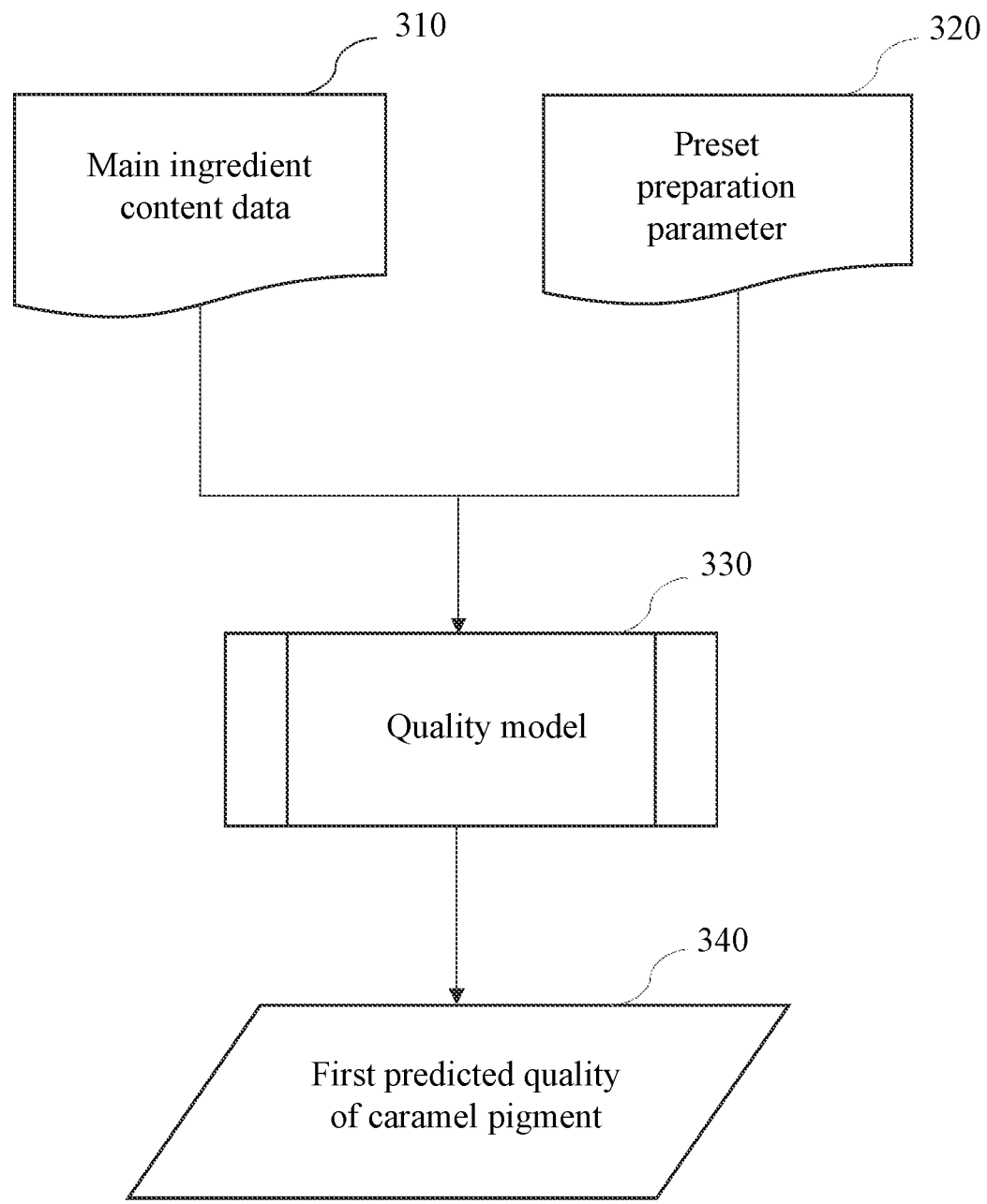
FIG. 3 is a schematic diagram illustrating an exemplary quality model according to some embodiments of the present disclosure.

FIG. 3 is a schematic diagram illustrating an exemplary quality model according to some embodiments of the present disclosure.

As shown in FIG. 3, in some embodiments, an input of a quality model 330 may include main ingredient content data 310 and a preset preparation parameter 320; and an output may include a first predicted quality 340 of a caramel pigment.

The preset preparation parameter 320 refers to a preset parameter for preparing the caramel pigment, and a preparation parameter may include an amount of catalyst, a reaction temperature, a reaction time, etc. For example, the preset preparation parameter may be "adding a compounded amino compound with a mass percentage of 6% to 12% to the concentrated raffinate liquid as a catalyst" as described above. For more content about the preset preparation parameter, please refer to elsewhere in the present disclosure.

In some embodiments, the processor may adjust the preset preparation parameter based on the first predicted quality 340 of the caramel pigment. For more details, please refer to the following descriptions.

In some embodiments, the quality model 330 may include a convolutional neural network model (CNN), a recurrent neural network model (RNN), or the like, or any combination thereof.

In some embodiments, the quality model may be obtained by training a large number of first training samples with a first label.

In some embodiments, the first training sample may be obtained based on historical preparation data for the caramel pigment of the browning reaction assembly 7. The first label may be an actual quality of the caramel pigment corresponding to the first training sample, which can be determined based on the historical preparation data for the caramel pigment.

In some embodiments, by using the quality model 330 to predict a quality index of the caramel pigment, the preset preparation parameter can be effectively and accurately adjusted subsequently, so that the quality of the caramel pigment can be better.

In some embodiments, if at least one of the first predicted quality of the caramel pigment does not meet a preset condition, the preset preparation parameter may be adjusted to determine the target preparation parameter.

In some embodiments, the determination of the target preparation parameter may include: determining a candidate preparation parameter set based on a difference between the first predicted quality and the target quality of the caramel pigment, wherein the candidate preparation parameter set may include at least one set of candidate preparation parameters; and performing at least one round of iterative update on the candidate preparation parameter set based on an evaluation score to determine the target preparation parameter.

A candidate preparation parameter refers to a preparation parameter that may be determined as the target preparation parameter. The candidate preparation parameter set refers to a set of candidate preparation parameters, and the candidate preparation parameter set may include the at least one set of candidate preparation parameters. For example, a preset preparation parameter (e.g., the amount of the catalyst) that may cause a deviation in the quality (i.e., a color rate, a red index, an absorbance at 610 nm, or the like.) of the caramel pigment may be determined based on historical experience, the preset preparation parameter (e.g., the amount of the catalyst) may be adjusted to obtain the at least one set of candidate preparation parameters to form the candidate preparation parameter set. The adjustment of the preset preparation parameter may be based on a deviation between a target quality index and the quality index. For example, the target color ratio may be lower than the color ratio, and the preset preparation parameter that causes the deviation may be determined according to the historical experience, and the preset preparation parameter may be determined to be larger or smaller, so as to adjust the preset preparation parameter.

The evaluation score may be configured to assess whether the candidate preparation parameter needs a parameter change. For example, a preset count of candidate preparation parameters with a highest evaluation score may be selected from the candidate preparation parameter set. Any parameter change may be performed on the preset count of candidate preparation parameters (e.g., a range of the reaction temperature may be reduced by half) to obtain a new candidate preparation parameter. The new candidate preparation parameter may be included in the original candidate preparation parameter set. The processor may remove an inferior candidate preparation parameter according to the evaluation score, and keep a count of parameters in the candidate preparation parameter set unchanged, thereby completing a round of iterative updates. For example, if the new candidate preparation parameter is included in the original candidate preparation parameter set, the count of candidate preparation parameters in the candidate preparation parameter set may increase, and the processor may remove a candidate preparation parameter with a lowest evaluation score in the candidate preparation parameter set to ensure that the count of sets of parameters in the candidate preparation parameter set does not change. When the candidate preparation parameter set satisfies an iteration completion condition, the iterative update may be completed. For example, the iteration completion condition may include that a count of iterative updates reaches a maximum, the evaluation score does not change, the evaluation score is higher than a preset score threshold, or the like.

In some embodiments, the processor may determine a candidate preparation parameter in a candidate preparation parameter set that achieves the iterative update as the target preparation parameter.

In some embodiments, by iteratively updating the candidate preparation parameter set to determine the target preparation parameter based on the evaluation score, the preparation parameter for preparing the caramel pigment may be ensured to be more accurate, thereby ensuring the high quality of the caramel pigment.

In some embodiments, the processor may determine the evaluation score in various ways. For example, the greater the difference between the predicted quality and the target quality, the lower an evaluation score of a candidate preparation parameter after an adjustment of a preset preparation parameter that caused the difference.

In some embodiments, the evaluation score may include a second predicted quality, a preparation cost, a quality stability level, or the like.

The second predicted quality may include the predicted quality distribution of caramel pigment in multiple regions in multiple devices, which may be represented by a mean value and effective value (a corresponding value after stirring well) of the multiple regions in the multiple devices. In some embodiments, the second predicted quality may be an output of the quality mode after the candidate preparation parameter is inputted into the quality model.

The quality stability level refers to a degree to which the quality of the caramel pigment remains stable.

In some embodiments, the quality stability level may be determined based on a predicted distribution of quality index in a second quality index. For example, in the second quality index, the more uniform the distribution of the predicted quality index in different devices (e.g., a concentration tank, a browning reactor), the greater the minimum value of the quality index (i.e., the higher the quality bottom line), and the higher the quality stability level. Uniformity of the distribution may be measured according to statistical indicators such as a standard deviation, a variance, and a difference between different devices.

The preparation cost refers to a cost of preparing the caramel pigment. For example, the preparation cost may include a time cost, an economic cost, or the like.

In some embodiments, the processor may determine the evaluation score based on the second quality index, the preparation cost, and the quality stability level according to a following formula (1):

$$P = \times Q - W2 \times C + W3 \times S, \qquad (1)$$

where, W1, W2, and W3 denote a proportion; Q denotes the second predicted quality; C denotes the preparation cost; S denotes the quality stability level. Proportion W1 of the second predicted quality may be the highest; proportion W2 of the quality stability level may be the second-highest; proportion W3 of the preparation cost may be the lowest.

In some embodiments, by determining the evaluation score based on the second quality index, the preparation cost, and the quality stability level, the efficiency and accuracy of iteratively updating the candidate preparation parameter set through the evaluation score subsequently may be improved.

In some embodiments, the detection device may further be configured to: obtain a sample of a processing caramel pigment in at least one sampling time point during the process of preparing the caramel pigment; detect the sample of the processing caramel pigment obtained in at least one sampling time point to obtain processing main ingredient content data during the process; send the processing main ingredient content data during the process to the processor. The processor may be configured to analyze the processing main ingredient content data during the process and determine a probability of preparation abnormality of a current reaction.

The sample of the processing caramel pigment refers to a sample of caramel pigment obtained by sampling during the process of preparation.

In some embodiments, the processing caramel pigment sample may be obtained in various ways. For example, a worker may sample the caramel pigment during the process of preparation at the sampling time point.

The sampling time point refers to the time point at which the caramel pigment is sampled during the process of preparation.

In some embodiments, the processor may determine at least one time point from a preset time period as the sampling time point.

In some embodiments, the determining the at least one sampling time point by the processor may include: determining a first sampling time point based on the main ingredient content data and the target preparation parameter; in response to a probability of preparation abnormality of the first sampling time point being below an abnormality risk threshold, a subsequent sampling time point may be determined. In some embodiments, the determining the subsequent sampling time point may include: from a second sampling time point, determining a next sampling time point based on a probability of preparation abnormality corresponding to a sample of the processing caramel pigment at a previous sampling time point.

In some embodiments, the processor may determine the first sampling time point by a vector retrieval based on the main ingredient content data and the target preparation parameter. For example, the processor may construct a vector to be matched based on the main ingredient content data and the target preparation parameter. The processor may search in a vector database based on the vector to be matched to obtain a reference vector whose vector distance from the vector to be matched satisfies a distance threshold, and determine a historical key time point corresponding to the reference vector as the first sampling time point. The vector database may be configured to store several historical vectors and historical key time points corresponding to the several historical vectors. The historical vector may be constructed based on historical main ingredient content data and a historical target preparation parameter. The key time point may include: a time point when a large-scale browning reaction starts, a time point when the large-area browning reaction ends, and a time point at which the browning reaction is normal or abnormal based on the main ingredient content data can be determined.

In some embodiments, the processor may determine the next sampling time point based on a difference between a probability of preparation abnormality at the previous sampling time point and the abnormality risk threshold. For example, the larger the difference, the closer the interval between the next sampling time point and the previous sampling time point, so an intervention and in-time adjustment may be ensured when an abnormality occurs during the process of preparation, avoiding a larger loss.

In some embodiments, by determining at least a subsequent sampling time point based on the main ingredient content data and the target preparation parameter, the sampling time point can be ensured to be representative, and ensure that the sample of the processing caramel pigment sampled subsequently can have relatively higher accuracy.

The processing main ingredient content data refers to main ingredient content data of the sample of the processing caramel pigment. In some embodiments, the main ingredient content data of the caramel pigment at the sampling time point may be represented by a component content of a processing reducing sugar.

In some embodiments, the detection device may use a conductivity meter to detect a conductivity rate of the sample of the caramel pigment to determine a component content of a reducing sugar.

The probability of preparation abnormality refers to a probability of abnormality during the process of preparation of the caramel pigment.

In some embodiments, the processor may determine the probability of preparation abnormality based on a historical preparation record. For example, in a historical preparation record corresponding to a component content of a same processing reducing sugar, a ratio of a count of abnormalities during the preparations of the caramel pigment to a total count of the preparations of the caramel pigment may be determined as the probability of preparation abnormality.

In some embodiments, the processor may determine a probability of production abnormality of a current browning reaction using a preparation process analysis model.

In some embodiments, an input of the preparation process analysis model may include the component content of the processing reducing sugar, the target preparation parameter, and the sampling time point; and an output may include the probability of preparation abnormality.

In some embodiments, the preparation process analysis model may be a convolutional neural network model (CNN), a recurrent neural network model (RNN), etc., or a combination thereof.

In some embodiments, the preparation process analysis model may be obtained by training a large number of second training samples with a second label.

In some embodiments, the second training sample may be obtained based on historical preparation data for the caramel pigment of the browning reaction assembly. The second label may be whether there is an abnormality in an actual preparation of the caramel pigment corresponding to the second training sample. The second label may be represented by 0 or 1, 0 indicating that there is no abnormality in the actual preparation; and 1 indicating that there is an abnormality in the actual preparation. The second label may be determined based on the historical preparation data for the caramel pigment.

In some embodiments, by using the preparation process analysis model to determine the probability of preparation abnormality, the accuracy and reliability of the probability of preparation abnormality can be effectively guaranteed.

In some embodiments, by sampling and detecting the main ingredient content data during the process of preparation of the caramel pigment, whether there are abnormalities in the preparation of the caramel pigment can be determined in advance, so that preventive measures can be taken to ensure a successful preparation of the caramel pigment.

The basic concept has been described above, obviously, for those skilled in the art, the above detailed disclosure is only an example and does not constitute a limitation to the present disclosure. Although not expressly stated here, those skilled in the art may make various modifications, improvements, and corrections to the present disclosure. Such modifications, improvements, and corrections are suggested in the present disclosure, so such modifications, improvements, and corrections still belong to the spirit and scope of the exemplary embodiments of the present disclosure.

Meanwhile, the present disclosure uses specific words to describe the embodiments of the present disclosure. For example, "one embodiment," "an embodiment," and/or "some embodiments" refer to a certain feature, structure, or characteristic related to at least one embodiment of the present disclosure. Therefore, it should be emphasized and noted that two or more references to "an embodiment" "one embodiment" or "an alternative embodiment" in different places in the present disclosure do not necessarily refer to the same embodiment. In addition, certain features, structures, or characteristics in one or more embodiments of the present disclosure may be properly combined.

In some embodiments, numbers describing the number of components and attributes are used. It should be understood that such numbers used in the description of the embodiments use the modifiers "about," "approximately," or "substantially" in some examples. Unless otherwise stated, the modifiers "about," "approximately," or "substantially" indicates that the stated figure allows for a variation of ±20%. Accordingly, in some embodiments, the numerical parameters used in the present disclosure and claims are approximations that can vary depending on desired characteristics of individual embodiments. In some embodiments, numerical parameters should take into account the specified significant digits and adopt the general digit reservation manner. Although the numerical ranges and parameters used in some embodiments of the present disclosure to confirm the breadth of the range are approximations, in specific embodiments, such numerical values should be set as precisely as practicable.

Each patent, patent application, patent application publication, and other material, such as article, book, specification, publication, document, etc., cited in the present disclosure is hereby incorporated by reference in its entirety. Historical application documents that are inconsistent with or conflict with the content of the present disclosure are excluded, and documents (currently or later appended to the present disclosure) that limit the broadest scope of the claims of the present disclosure are excluded. It should be noted that if there is any inconsistency or conflict between the descriptions, definitions, and/or terms used in the accompanying materials of the present disclosure and the contents of the present disclosure, the descriptions, definitions, and/or terms used in the present disclosure shall prevail.

Finally, it should be understood that the embodiments described in the present disclosure are only used to illustrate the principles of the embodiments of the present disclosure. Other modifications are also possible within the scope of the present disclosure. Therefore, by way of example and not limitation, alternative configurations of the embodiments of the present disclosure may be considered consistent with the teachings of the present disclosure. Accordingly, embodiments of the present disclosure are not limited to the embodiments explicitly introduced and described in the present disclosure.

What is claimed is:

1. A method for co-producing a xylitol and a caramel pigment by utilizing a xylose mother liquid, comprising following steps:
    step one, transporting a raw material of the xylose mother liquid in a raw material tank to a filter via a pipeline for filtering impurities to obtain a filtered raw material of the xylose mother liquid, and transporting the filtered raw material of the xylose mother liquid to a nanofiltration membrane device for a decolorizing process to obtained a decolorized xylose mother liquid;
    step two, transporting the decolorized xylose mother liquid to a first ion exchange device for a desalting process to obtain an ion exchange liquid;
    step three, transporting the ion exchange liquid to a chromatographic separation device for a chromatographic separation process and obtaining an extracted liquid and a raffinate liquid after the chromatographic separation process, wherein a xylose component content of the extracted liquid is higher than a xylose component content of the raffinate liquid, performing a refined hydrogenation process on the extracted liquid by a refined hydrogenation assembly to obtain a crystal xylitol with a purity over 99%, and performing a browning reaction process on the raffinate liquid by a browning reaction assembly to obtain the caramel pigment; wherein
    in the step one, a mass percentage concentration of a dry matter of the xylose mother liquid is 50~60 wt %, wherein, in the dry matter, a content of glucose is 12~18 wt %, a content of xylose is 40~50 wt %, a content of arabinose is 17~23 wt %, a content of mannose is 10~22 wt %, and a content of galactose is 0~6 wt %;
    in the step one, during the decolorizing process, an operating temperature of the nanofiltration membrane device is 40° C. to 48° C., an operating pressure of the nanofiltration membrane device is 25 bar to 35 bar, and a yield rate of the nanofiltration membrane device reaches 90% to 98%;
    in the step two, during the desalting process, an electrical conductivity rate is controlled to be smaller than 50 us/cm, and a yield rate reaches 90% to 98%;
    the refined hydrogenation process in the step three includes: transporting the extracted liquid after evaporation and concentration to a crystallization tank for crystallization to obtain a crystal xylose, dissolving the crystal xylose with water to obtain a xylose liquid, transporting the xylose liquid to a hydrogenation reactor for a hydrogenation reaction to obtain a xylitol solution, settling the xylitol solution to remove a catalyst after the hydrogenation reaction, adopting a second ion exchange device for performing the desalting process on a supernatant after settling the xylitol solution to obtain a desalted solution, performing vacuum evaporation and concentration on a desalted solution by using a vacuum crystallization assembly, and performing vacuum boiling of sugar and crystallization to precipitate a crystal, and obtaining the crystal xylitol by performing a centrifugation operation and a drying operation on the crystal;
    in the step three, while dissolving the crystal xylose with water, a refraction of the xylose liquid is 50% to 60% and a pH value of the xylose liquid is 5.00 to 7.00, a nickel catalyst with a mass percentage of 0.01% to 0.02% is added into the xylose liquid, a reaction temperature is controlled to be between 130° C. to 140° C. and a steam pressure is controlled to be above 0.4 MPa, and the hydrogenation reaction is performed for 60 minutes to 120 minutes; the raffinate liquid is concentrated to the refraction being between 75% to 85% and a pH value is adjusted to be between 7.00 to 9.00, a compounded amino compound with a mass percentage of 6% to 12% is added as a catalyst, and a reaction temperature of the browning reaction is controlled to be between 120° C. to 140° C. and a time of the browning reaction is 60 minutes to 240 minutes; and
    the browning reaction process in the step three includes: obtaining a caramel pigment liquid by performing a concentration process, the browning reaction process, and a filtering process on the raffinate liquid, wherein a red index of the caramel pigment liquid is over 7, and an absorbance of the caramel pigment at 610 nm is over 0.07.

2. The method according to claim 1, wherein the method adopts a system for co-producing the xylitol and the caramel pigment by utilizing the xylose mother liquid, the system comprising the raw material tank, the filter, the nanofiltration membrane device, the first ion exchange device, and the chromatographic separation device, the refined hydrogenation assembly, and the browning reaction assembly that are connected via a pipeline sequentially, the raw material tank is configured to store the xylose mother liquid, the filter is configured to filter impurities in the xylose mother liquid, the nanofiltration membrane device is configured to obtain a retentate liquid and a permeation liquid respectively by decolorizing the xylose mother liquid that flows through the nanofiltration membrane device, the retentate liquid being a pigment liquid, and the permeation liquid being a decolorized liquid, the first ion exchange device is configured to obtain the ion exchange liquid by desalting the decolorized liquid that flows through the first ion exchange device, the chromatographic separation device is configured to separate the extracted liquid and the raffinate liquid from the ion exchange liquid that flows through the chromatographic separation device, the refined hydrogenation assembly is configured to perform the refined hydrogenation process on the extracted liquid to prepare the crystal xylitol and the browning reaction assembly is configured to perform a browning reaction process on the raffinate liquid to prepare the caramel pigment; the refined hydrogenation assembly includes an evaporation and concentration device, the crystallization tank, a crystal xylose storage tank, a dissolving tank, the hydrogenation reactor, a second ion exchange device, and the vacuum crystallization assembly, the evaporation and concentration device is configured to concentrate the extracted liquid, the crystallization tank is configured to obtain the crystal xylose by crystallizing a xylose, the crystal xylose storage tank is configured to store the crystal xylose, the dissolving tank is configured to dissolve the crystal xylose into the xylose liquid and store the xylose liquid, the hydrogenation reactor is configured to generate the xylitol solution by performing a hydrogenation reduction reaction on the xylose liquid, the second ion exchange device is configured to remove anions and cations from the xylitol solution, and the vacuum crystallization assembly is configured to obtain the crystal xylitol by crystallizing the xylitol solution that is processed by the second ion exchange device; the browning reaction assembly includes a concentration tank, a browning reaction reactor, and a browning reaction filter, the concentration tank is configured to concentrate the raffinate liquid to a preset concentration range and store a concentrated raffinate liquid, the browning reaction reactor is configured to obtain the caramel pigment by performing the browning reaction process on the raffinate liquid, and the browning reaction filter is configured to filter solid impurities in the caramel pigment.

* * * * *